US 8,287,506 B2

(12) United States Patent
Wells et al.

(10) Patent No.: US 8,287,506 B2
(45) Date of Patent: Oct. 16, 2012

(54) APPARATUS AND METHODS FOR CONTROLLING TISSUE OXYGENATION FOR WOUND HEALING AND PROMOTING TISSUE VIABILITY

(75) Inventors: Michael C. Wells, San Antonio, TX (US); Mark Parker, Houston, TX (US); Daniel J. Clarius, Missouri City, TX (US); Andrew Parker, Missouri City, TX (US); Faraidoon Pundole, Sugar Land, TX (US); Tom Woods, Friendswood, TX (US)

(73) Assignee: Electrochemical Oxygen Concepts, Inc., San Antonio, TX (US)

( * ) Notice: Subject to any disclaimer, the term of this patent is extended or adjusted under 35 U.S.C. 154(b) by 695 days.

(21) Appl. No.: 12/288,873

(22) Filed: Oct. 24, 2008

(65) Prior Publication Data

US 2009/0112170 A1    Apr. 30, 2009

Related U.S. Application Data

(60) Provisional application No. 61/000,695, filed on Oct. 26, 2007.

(51) Int. Cl.
*A61F 13/00* (2006.01)

(52) U.S. Cl. .......................................... 604/304; 604/23
(58) Field of Classification Search .................. 604/23, 604/19, 65, 67, 290, 304, 305; 128/204.21; 607/50

See application file for complete search history.

(56) References Cited

U.S. PATENT DOCUMENTS

| | | | |
|---|---|---|---|
| 3,489,670 A | 1/1970 | Maget | |
| 5,578,022 A * | 11/1996 | Scherson et al. | 604/304 |
| 5,788,682 A * | 8/1998 | Maget | 604/290 |
| 6,010,317 A | 1/2000 | Maget et al. | |
| 6,171,368 B1 | 1/2001 | Maget et al. | |
| 2003/0083610 A1* | 5/2003 | McGrath et al. | 604/24 |
| 2006/0225737 A1* | 10/2006 | Iobbi | 128/204.21 |
| 2006/0287632 A1* | 12/2006 | Sarangapani | 604/304 |
| 2011/0054388 A1* | 3/2011 | Wells et al. | 604/23 |

* cited by examiner

*Primary Examiner* — Tatyana Zalukaeva
*Assistant Examiner* — Benedict L Hanrahan
(74) *Attorney, Agent, or Firm* — Haynes & Boone, LLP; William B. Nash; Joe Mencher

(57) ABSTRACT

A non-invasive tissue oxygenation system for accelerating the healing of damaged tissue and to promote tissue viability is disclosed herein. The system is comprised of a lightweight portable electrochemical oxygen concentrator, a power management system, microprocessors, memory, a pressure sensing system, a temperature monitoring system, oxygen flow rate monitoring and control system, a display screen and key pad navigation controls as a means of providing continuous variably controlled low dosages of oxygen to a wound site and monitoring the healing process. A kink resistant oxygen delivery tubing, whereby the proximal end is removably connected to the device and the distal end with holes or a flexible, flat, oxygen-permeable tape is positioned on the wound bed as a means of applying oxygen to the wound site. The distal end of the tube is in communication with the electrochemical oxygen concentrator and wound monitoring system to communicate temperature and oxygen partial pressure information. A moisture absorbent dressing is positioned over the distal end of the tubing on the wound site and a reduced moisture vapor permeable dressing system is positioned whereby covering the moisture absorbent dressing, distal end of tubing and wound site creating a restricted airflow enclosure. The restricted airflow enclosure allows the out-of-the-way control and display unit to provide a controlled hyperoxia and hypoxia wound site for accelerated wound healing.

10 Claims, 6 Drawing Sheets

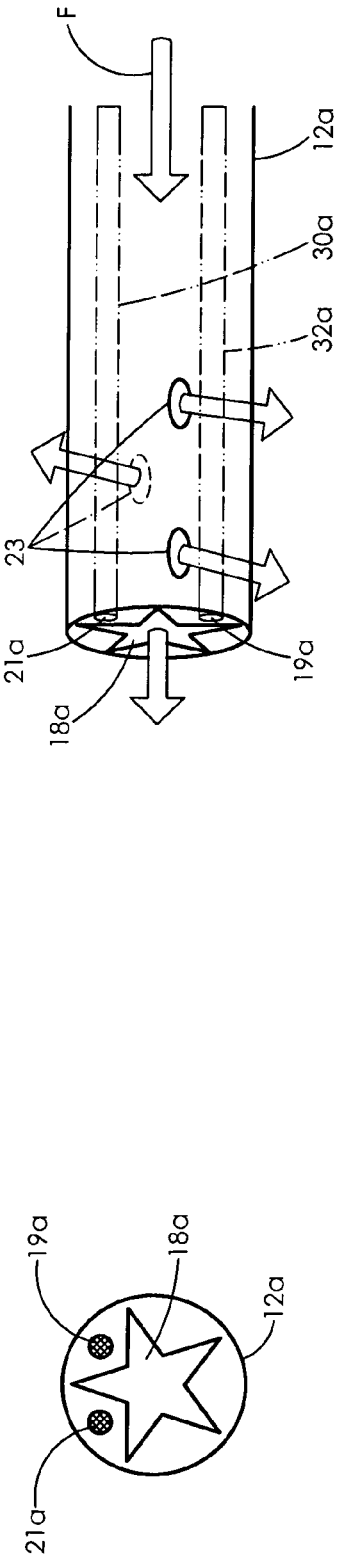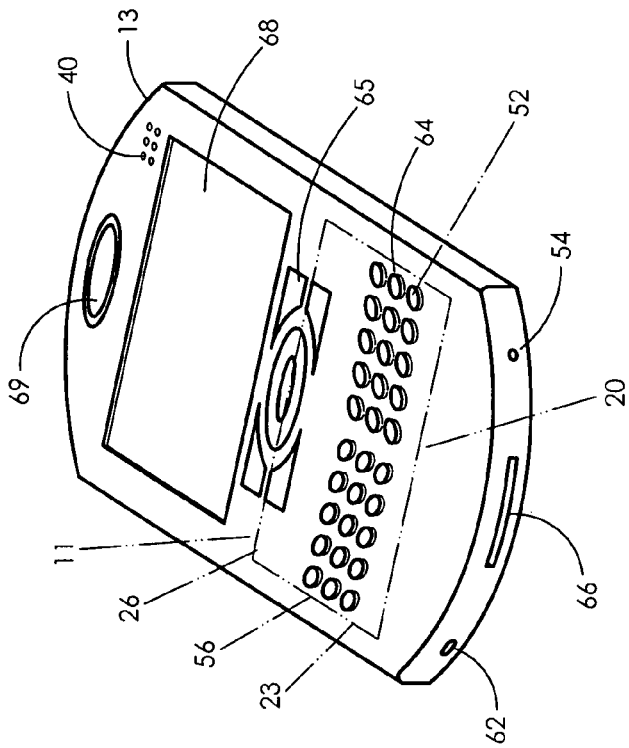

APPARATUS AND METHODS FOR CONTROLLING TISSUE OXYGENATION FOR WOUND HEALING AND PROMOTING TISSUE VIABILITY

This application claims the benefit of and priority from U.S. Provisional Patent Application Ser. No. 61/000,695, filed Oct. 26, 2007.

BACKGROUND OF THE INVENTION

This invention relates to tissue treatment systems, specifically to non-invasive tissue oxygenation systems for accelerating the healing of damaged tissue and promoting tissue viability. When skin is damaged a wound results and a four phase healing process begins. Optimal metabolic function of these cells to repopulate the wound requires that oxygen be available for all phases of wound healing. The more layers of tissue that are damaged the greater the risk for complications to occur in the wound healing process.

Difficult-to-heal wounds encounter barriers to the wound healing process and typically experience delays in one or more of the last three phases of wound healing. One of the most common contributing factors to venous leg ulcers, diabetic foot ulcers and pressure ulcers experiencing delays in the healing process is the problem of chronic wound ischemia. Chronic wound ischemia a pathological condition that restricts blood supply, oxygen delivery and blood request for adequate oxygenation of tissue, inhibiting normal wound healing.

In practice the standard of care for treating difficult-to-heal wounds typically involves the use of an advanced wound dressing or combination of advanced wound dressings providing a dressing treatment system. An advanced dressing is positioned on the wound site or on the wound site and the surrounding intact skin providing a wound site enclosure. An advanced wound dressing is typically comprised of materials having properties for promoting moist wound healing, managing wound exudate and helping control wound bioburden. The typical material components in combination further include properties for providing limited moisture vapor permeability. The lower the dressing's moisture vapor permeability or more occlusive the dressing the lower the amount of ambient air and the respective lower amount of oxygen is thereby available to the wound bed. 100% oxygen exerts a partial pressure of 760 mm Hg. Ambient air is comprised of about 21% oxygen thereby exerting a partial pressure of oxygen at about 159 mm Hg. A typical advanced wound dressing or wound dressing system comprised of lower moisture vapor permeable materials impacts the available oxygen for the wound site thereby limiting the partial pressure of oxygen at the enclosed wounds site at about 10 mm Hg to 60 mm Hg. Fresh air is provided to the wound site only when the dressing is changed. A dressing may remain covering the wound site for up to seven days before a dressing change is required. The moisture vapor permeability property of an advanced wound dressing providing a reduced oxygen wound environment thereby works against the optimal metabolic function of cells to repopulate the wound which requires that oxygen be available for all phases of wound healing.

Prior art methods of tissue oxygenation for difficult-to-heal wounds include topical hyperbaric oxygen applied intermittently or continuously. Intermittent topical hyperbaric oxygen is a method of tissue oxygenation comprising of a sealed extremity or partial body chamber and a connected source of high flow pure oxygen whereby the affected limb or affected body area is positioned in a sealed extremity chamber or partial body chamber so that the oxygen source supplying the chamber is providing the patient topically up to 100% oxygen at flow rates that may exceed 300 liters per hour pressurizing the interior of the chamber up to 1.05% normal atmospheric pressure thereby increasing the available oxygen for cellular processing at affected wound site. During the oxygen application, the partial pressure of oxygen exerted inside the topical or partial body chamber may attain 798 mm Hg. Topical hyperbaric oxygen is applied for about 90 minutes. Prior art also teaches a plurality of methods to apply topically hyperbaric oxygen intermittently. A partial body chamber for treating sacral wounds has been described in U.S. Pat. No. 4,328,799 to LoPiano (1980) whereby oxygen is applied from a stationary supply tank into the interior of the chamber through connected tubing. A similar method of applying topical hyperbaric oxygen is described in U.S. Pat. No. 5,478,310 to Dyson-Cantwell (1995) whereby oxygen is applied from a stationary supply tank into the interior of the disposable extremity chamber through connected tubing. These and similar methods of applying intermittent topical hyperbaric oxygen are restrictive, cumbersome, can only supply oxygen to the affected area intermittently with no systemic application, and can only be applied with a minimal increase in atmospheric pressure (about 5%). Therefore the effect of the oxygen therapy on the wound can be minimal which is evidenced by the lack of commercial success from topical hyperbaric oxygen extremity chambers.

Both U.S. Pat. No. 5,578,022 to Scherson (1996) and U.S. Pat. No. 5,788,682 to Maget (1998) describe disposable devices utilizing transmission of gases in ionic form through ion specific membranes to apply supplemental oxygen directly to the wound bed. These devices are described as battery powered, disposable, oxygen producing bandages and methods that are applied directly over the wound. They both include electrochemical oxygen generation using variations of the same 4 electron formula originally developed for NASA in U.S. Pat. No. 3,489,670 to Maget (1970). The amount of oxygen that can be applied to the wound is typically 3 milliliters per hour. Specific oxygen flow rates are generated by means of corresponding specific, preselected battery sizes and specific prescribed amperages. Prior art describes disposable devices are either "on or off." The prior art describes disposable devices without means to sense temperature changes in the wound site oxygen environment. Prior art does not provide a means to deliver a varying (adjustable) oxygen flow rate without requiring the patient to obtain and apply a new device with a new battery having a specific amperage. Additional limitations are also associated with the use of a fixed non-variable oxygen flow rate.

No prior art low dose tissue oxygenation device provides continuous oxygen adjustability to a patient's wound(s) creating a controlled hyperoxia and hypoxia wound environment for damaged tissue to accelerate wound healing and promote tissue viability. Specifically, nothing in the prior art teaches continuous oxygen adjustability based on actual flow rate, partial pressures at the wound site, and temperatures at the wound site.

SUMMARY OF THE INVENTION

The invention is an improved low dose tissue oxygenation device and wound monitoring system. The present invention generally comprises an oxygen delivery tube for placement at the wound bed and a wound dressing covering the tubing and wound site for restricted air flow enclosure. The tubing may have multiple holes at or near the distal end of the tubing. The tubing may include a generally flat, flexible, oxygen-permeable tape or membrane section attached at the distal end of the tube. The tubing may be flexible with a kink resistant inner lumen. The tubing may have a temperature sensor. The tubing may have a pressure sensor. The tubing may include a partial pressure of oxygen sensor. The proximal end of the tubing is connected to a source of oxygen. The proximal end of the tubing may have a port Leur-type locking mechanism for an airtight seal during application of the oxygen and for removal from the oxygen source during application a dressing. A source of oxygen is in communication with the proximal and distal ends of the tube. A source of oxygen may be an electrochemical oxygen concentrator supplied by alternating or direct current, a power management device and its power management protocol. The variable electrochemical oxygen concentrator is used in accordance with the present invention by varying the oxygen flow rate to meet varying target parameters at the wound site. The oxygen flow rate is adjusted by a system that periodically or continuously monitors the wound bed pressure and temperature environment or the tubing pressure and adjusting the oxygen flow rate in accordance to target set points. Adjusting oxygen flow in response to monitored changes in wound site oxygen and target oxygen pressure and temperature protocols provides a controlled hyperoxia wound environment which may shorten the healing process.

In some embodiments, the device may have a backlight display terminal or touch screen liquid crystal display, a data input key pad or device function control buttons, a wound temperature monitoring system, a battery or oxygen pressure alarm system, a digital camera, a patient data input and memory system and/or a data port or wireless data access.

BRIEF DESCRIPTION OF THE DRAWINGS

A more complete understanding of the present disclosure and advantages thereof may be acquired by referring to the following description taken in conjunction with the accompanying figures, wherein:

FIG. 2A is an end view of another embodiment of the tubing of the present invention.

FIG. 3 is side elevation view of the distal end of the oxygen delivery tubing of the embodiment of FIG. 2A of the present invention FIG. 4 is a perspective view of a handset of the present invention.

Figure 1:
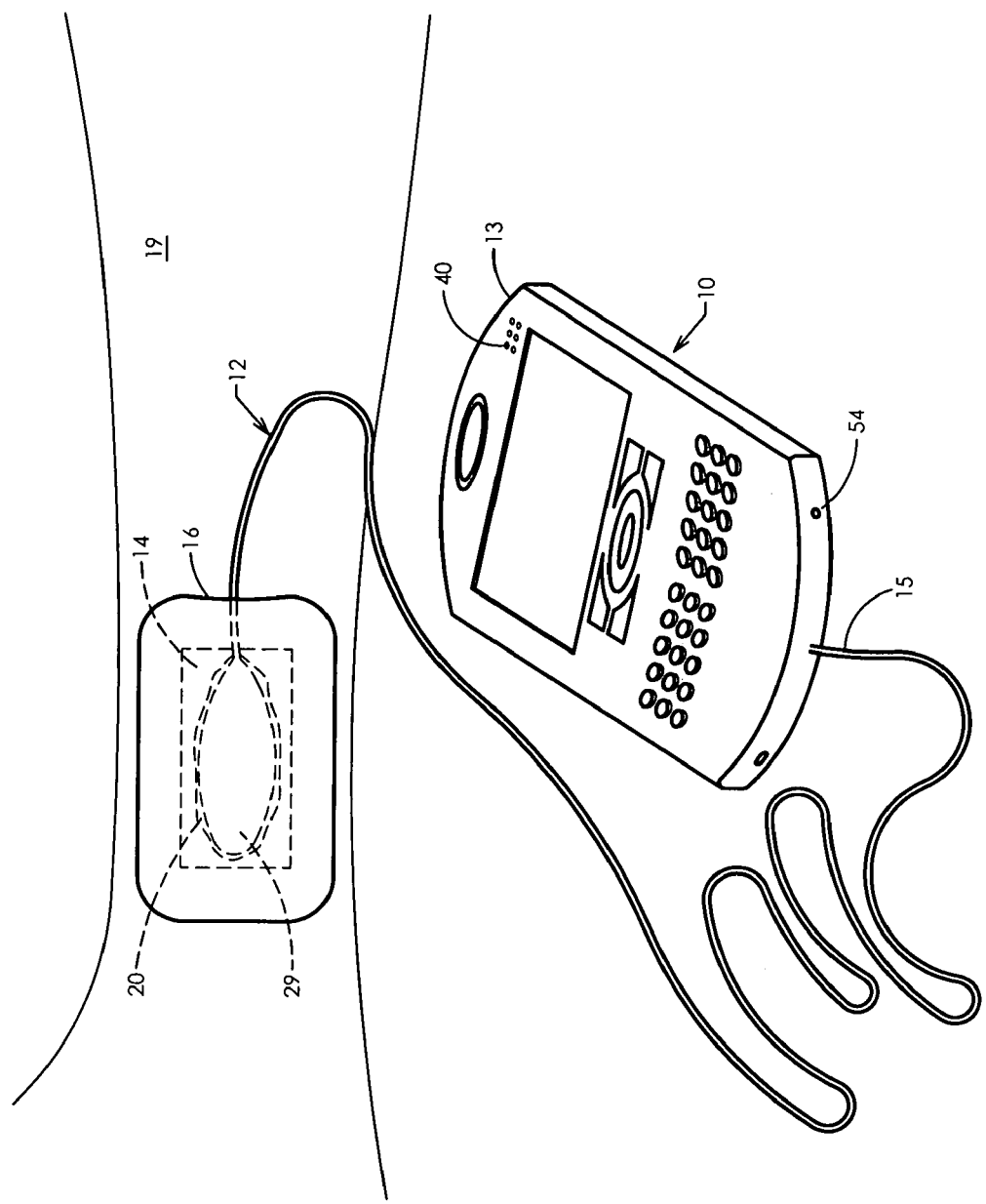
FIG. 1 is a perspective view of an embodiment of a tissue oxygenation system of the present invention.

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

A preferred embodiment of the present invention, tissue oxygenation system for the healing of damaged tissue and to promote tissue viability, will now be described in detail with reference to the figures.

FIG. 1 is a perspective view of several primary components of the present invention according to the preferred embodiment. The present invention includes a monitoring unit 10, an electrochemical oxygen concentrator 11, oxygen delivery tubing 12, moisture absorbent dressing 14, and vapor dressing 16. Preferably, oxygen delivery tubing 12 is connected at the proximal end 15 of the long, kink resistant tubing to the monitoring unit 10. The monitoring unit 10 has a small, lightweight housing which is portable and may be discretely worn by the patient in a pocket or attached to a belt.

The monitoring unit 10 includes within the housing 13 a microprocessor 58 (see FIGS. 5 and 7), a power management system 52, pressure 56 and temperature 57 sensor interface(s), a flow rate sensor 54, an input port 62 and a user entry port 66. The electrochemical oxygen concentrator 11 is disposed within the housing 13. The microprocessor 58 functions to control power, collect various readings from the flow, pressure, and temperature sensors controls ionic purification of room air by the electrochemical oxygen concentrator for delivery to the tubing, and controls the informational display on the monitoring unit 10. Preferably, the microprocessor 58 is capable of receiving data through the user entry port and the input port, including information related to specific patients and re-programming information if there is a system malfunction with the device.

Figure 1A:
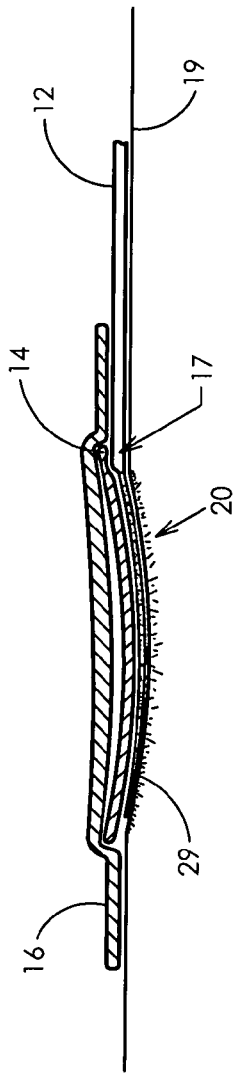
FIG. 1A is a cross section view of a wound site showing a distal end of a oxygen delivery tube of the present invention
Figure 2:
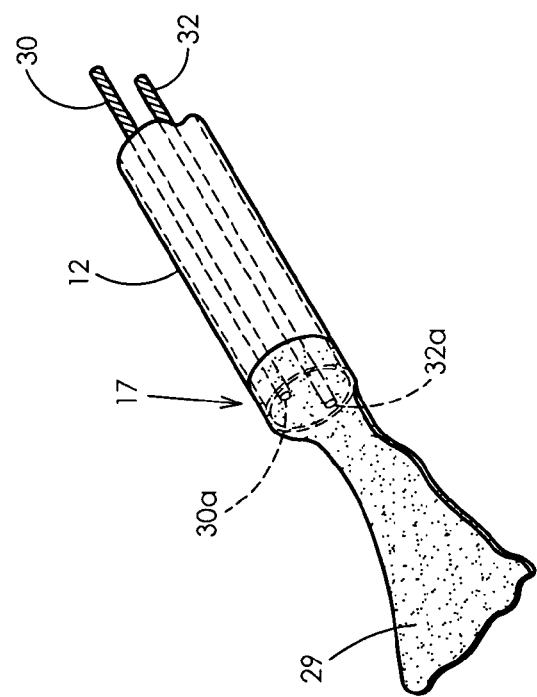
FIG. 2 is a side perspective view of the distal end of an embodiment of the tubing of the present invention showing a generally flat, flexible, oxygen-permeable tape or membrane section affixed to the tubing.

As may be further seen in FIGS. 1A and 2, the distal end 17 of the tubing 12 has a soft, flexible, oxygen permeable tape or membrane section 29 placed on the damaged tissue or wound site 20 of a patient's limb 19 covered with a moisture absorbent dressing 14 and further covered by a reduced vapor pressure, permeable, occlusive dressing 16.

In a first embodiment, oxygen is delivered to the wound site 20 through a kink-resistant tube 12 connected at the proximal end 15 to the outlet of the oxygen concentrator at the monitor unit housing. On the distal end 17 of the tubing 12 is connected soft, flexible oxygen-permeable flat tape or membrane 29. Extending through the lumen of the tube are several sensor wires 30 and 32. These wires communicate from temperature sensor 30a and oxygen partial pressure sensor 32a disposed at the wound site to temperature 57 and pressure 56 transducers in the monitoring unit with the transducers providing input to the microprocessor 58 as would be understood by one of ordinary skill in the art.

Alternatively, tubing 12a (FIG. 2A) preferably has several lumens, pressure 19a and temperature 21a sensors, and other such sensors as may be required to effectively monitor wound treatment, disposed therein. Specifically, FIG. 2A illustrates an end view of the tubing 12a, and depicts a tubing with a length capable of connecting to the output side of electrochemical oxygen concentrator 11 housed within monitoring unit 10. Such tubing lengths allow the monitoring unit to be worn discretely and continuously deliver oxygen to the wound site 20. An inner lumen, or bore 18a, of the tubing is a star like configuration to prevent kinking of the tubing and still allows oxygen flow if bent. The pressure sensor 19a such as, example, an oxygen partial pressure sensor, at the wound site is disposed within the tubing and is in communication with a pressure monitoring system including transducer 58 allowing for oxygen flow rate adjustment, visual pressure display, and out of range alarm. A temperature sensor 21a is also disposed within the tubing at the wound site 20 and is in communication with a temperature monitoring system including transducer 57 allowing for visual display of temperature, an out of range alarm, and allowing for oxygen adjustment via the microprocessor 58 as is appropriate.

FIG. 3 is a side view of the distal end of alternative tubing 12a, which includes a plurality of holes 23 formed along the side of the distal end of the tubing to aid in the delivery of oxygen to the wound. In use, the oxygen flows F through the tubing to the wound site and may enter the wound bed through the multiple holes 23. The oxygen may also flow through the distal end of star shaped lumen 18a, however, the multiple holes at the distal end of the tubing allow for improved flow of oxygen to the wound site 20.

FIG. 1A shows a wound site 20, with the distal end 17 of the oxygen delivery tubing 12 having the oxygen distribution tape 29 placed over the wound site 20. The tape 29 is placed centrally on the wound site for optimal delivery of oxygen to the damaged tissue. A moisture absorbent dressing 14 is placed at the wound site covering the tape end of the oxygen delivery tubing 12 and wound site. One skilled in the art will appreciate that moisture absorbent dressing is typical standard of care protocol for a difficult-to-heal wound. A reduced moisture vapor permeable dressing 16 covers the moisture absorbent dressing 14, tape end of tubing 12 and wound site 20, creating a restricted airflow enclosure. Preferably the reduced moisture vapor permeable dressing 16 is transparent and may be described to as an occlusive dressing. The occlusive dressing traps the oxygen over the wound site to create and maintain oxygen rich environment. The local partial pressure of oxygen at the wound site 20 may be increased from a low range of 10 to 60 mm Hg to an oxygen rich environment range of 200 to 760 mm HG. The increased available oxygen is metabolized at the cellular level and will stimulate an increase in growth factors, epithelialization, granulation tissue, glycosaminoglycan production, and collagen synthesis. The oxygen partial pressure at the wound site is communicated to the pressure monitoring transducer 57 in the housing 13. The transducer supplies data to the microprocessor 58 which controls the power flow (amperage) to the concentrator 11. The concentrator may increase or decrease the $O_2$ flow rate.

Figure 5:
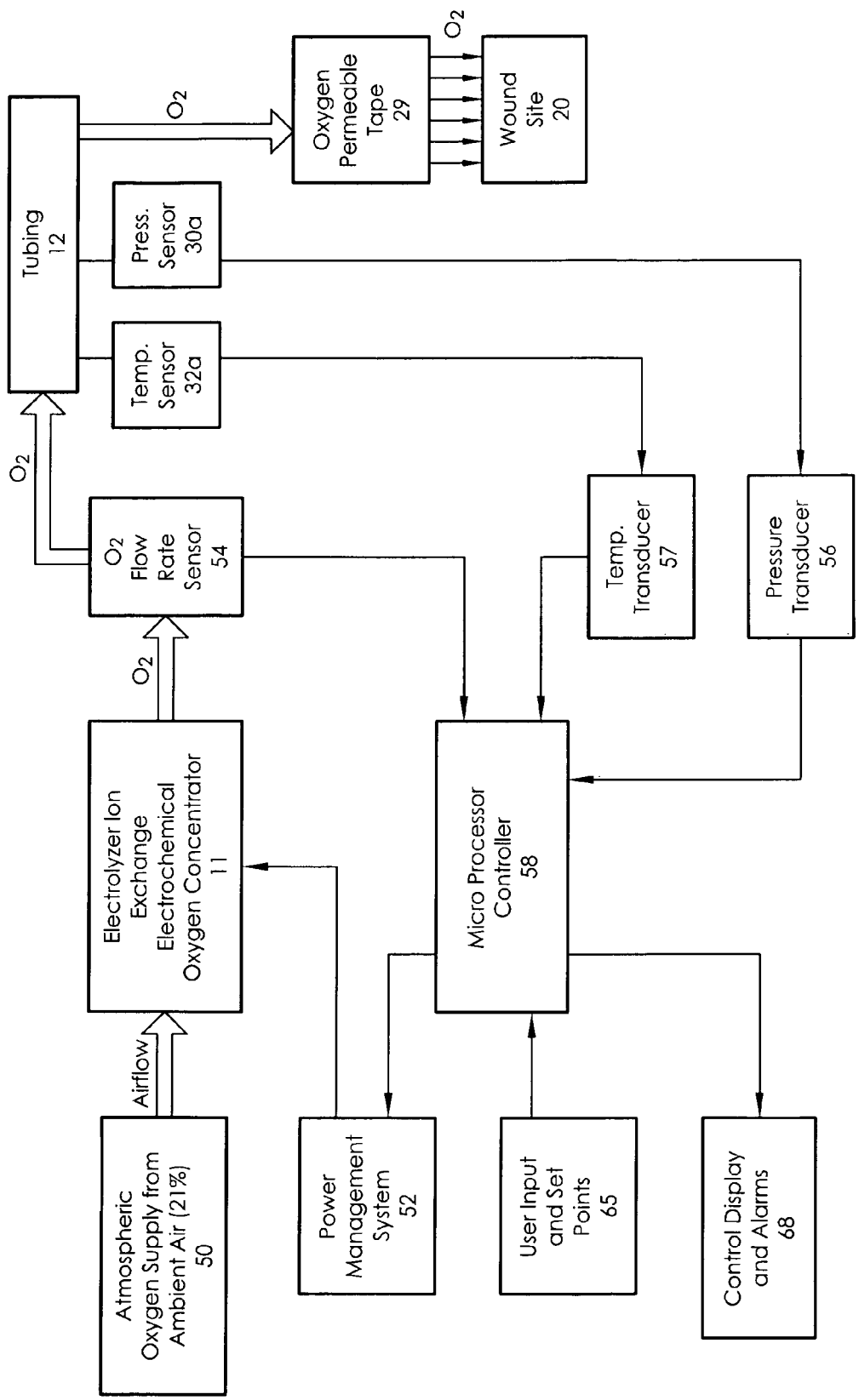
FIG. 5 is a flow chart illustrating the process of the present invention.

FIG. 4 is a perspective view of a handset housing the major components of the present invention. FIG. 5 is a flow chart of the present invention.

As shown in FIGS. 4 and 5, in use, the monitor housing 13 draws in room air 50 with about 21% oxygen through the air inlet 40 by means of an electrochemical process. The room air passes through an ion exchange oxygen concentrator 11, which concentrates the oxygen level of the room air to create a mixture that is 99% pure oxygen. The power management system 52 controls the electrical current supplied to the ion exchange oxygen concentrator 11, thereby making the oxygen flow rate conform to the amount of current supplied to the ion exchange oxygen concentrator, i.e., increasing electrical current increases the electrochemical process and thereby increases the respective oxygen flow rate to the wound site 20 and decreasing the electrical current decreases the electrochemical process thereby decreasing the respective oxygen flow rate to the wound site. It should be noted that the power management system 52 includes lithium batteries (7.4 v) and a regulator which varies the amperage over a range from approximately 15 milliamps to approximately 150 milliamps. This range of current variation results in $O_2$ flow rates in the range of approximately 1.0 milliliters/hour to approximately 15.0 milliliters/hour.

The concentrated $O_2$ then exits the housing through the oxygen delivery port 54. The proximal end 15 of the oxygen delivery tubing 12 is connected with an oxygen delivery port 54 with Leur-type locking fitting. The locking fitting is engaged to maintain an airtight seal with the tubing.

As illustrated in FIGS. 2 and 5, a pressure sensor 30a or 19a and a temperature sensor 32a/21a in the tubing 12 or 12a are in communication with a pressure transducer 56 and a temperature transducer 57. The microprocessor 58 communicates with the power management system 52, the pressure transducer 56, and temperature transducer 57 adjusting the oxygen flow rate (sensed at sensor 54) to the wound site per programmed algorithms to optimally meet changes in the patients oxygen wound healing requirements.

Figure 6:
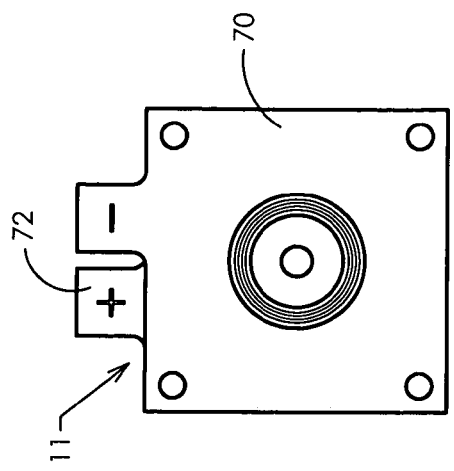
FIG. 6 is a top plan view of the electrolyzer/concentrator of the present invention.
Figure 6A:
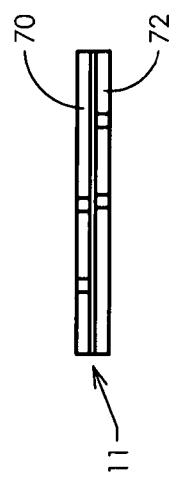
FIG. 6A is a side elevation plan view of the electrolyzer of FIG. 6.
Figure 6B:
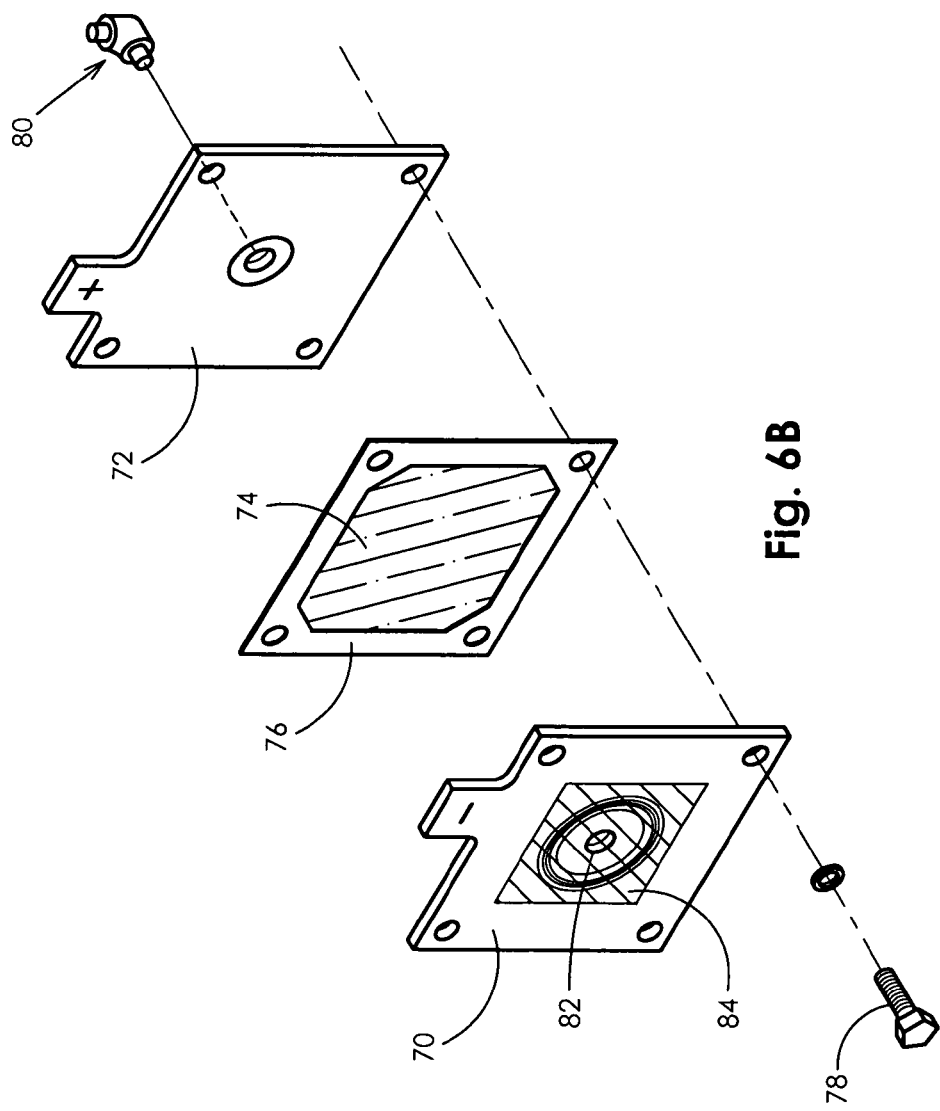
FIG. 6B is an exploded perspective view of the eletrolyzer of FIG. 6.

Turning to FIGS. 6-6B, the electrochemical oxygen generator/concentrator 11 is illustrated. FIG. 6 is a top plan view of concentrator 11 showing the cathode plate 70 overlaying the anode plate 72. FIG. 6A is a side elevation view of the concentrator 11.

Each of the charged plates has a carbon backed metalized substrate with a titanium mesh plated on the carbon membrane. This provides a complete coverage area for electrical conductance to a Nafion® oxygen transfer membrane. Nafion® is a registered trademark of DuPont and is a sulfonated tetrafluroethylene copolymer. Nafion® is well known in the art as a proton conductor for proton exchange membranes (PEM). A Nafion 212 membrane is preferred in the present invention.

FIG. 6B is an exploded perspective view of the concentrator 11. The PEM membrane 74 is compressed fully (40-60 ft-lbs force) between the cathode 70 and the anode 72. To provide proper sealing of the concentrator, a gasket seal 76 may be utilized with flange bolting 78. A 304L stainless steel needle discharge valve 80 with viton seats is machined for attachment into the anode plate 72 using a viton O-ring (not shown).

Electrical contact and transfer to the plates is accomplished by attaching a copper strip to the titanium mesh substrate. The compressive force applied provides the necessary adhesion to the surfaces of the two metals. The strips are then attached to the charge plates with epoxy.

Ambient air enters the concentrator through inlet 82 which is covered by a polarized membrane 84 which allows water vapor to pass in one direction only and maintain the encapsulation of other gases (mainly hydrogen). The preferred membrane 84 in the present invention is a Gore-Tex® fabric. (Gore-Tex® is the registered trademark of W. L. Gore & Associates.) Concentrated $O_2$ is discharged out discharge valve 80 which communicates with discharge 54 in housing 13.

Figure 7:
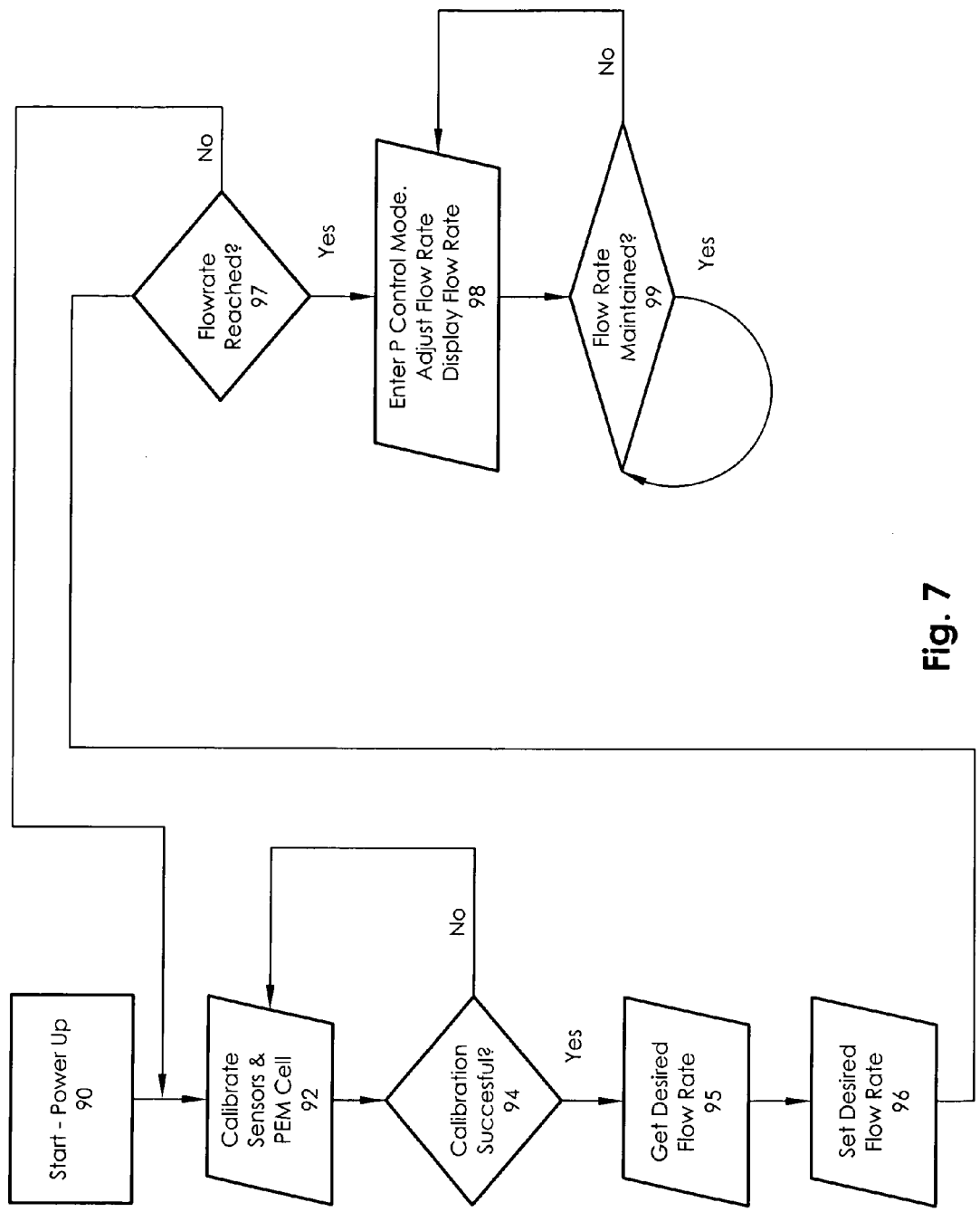
FIG. 7 is a processor firmware flow chart of the present invention.

A firmware flow chart for the present invention is illustrated in FIG. 7. When the monitoring unit 10 is started or powered up 90, the microprocessor 58 calibrates 92 all sensors and the PEM cell. Because every PEM cell and each sensor has its own particular functional characteristics, the present invention calibrates the sensors and cell to ensure precise flow rates.

If the calibration is successful 94, then the microprocessor gets the desired 95 flow rate from the user. The microprocessor calculates the voltage and current to output from the PEM the set desired flow rate 96. The microprocessor receives input from the flow rate sensor 54 and determines if the set flow rate has been reached 97, if not the processor again seeks to recalibrate the sensors and the PEM cell. If the set flow rate is reached 97, then the microprocessor enters a proportional control mode 98. The flow rate may be adjusted based upon input from the temperature monitoring system and the pressure monitoring system. The microprocessor also displays the flow rate and the temperature on the monitor display screen 68.

In the proportional control mode, the microprocessor continuously tests the actual flow rate to ensure that it is maintained 99 using a feedback loop which looks at variations in sensor and PEM cell efficiencies.

In another embodiment of the invention a wound monitoring system is contemplated. Patient data and therapy commands are communicated to the device by the care giver or patient for processing by means of a data input key pad 64 and function control buttons 65. A data port 66 may be used to upload or download data. The monitoring system allows for collection and monitoring of key medical parameters to aid the caregiver in managing the patient care and potentially accelerate the healing process with improved access to more data. Available patient data and device functions are displayed and where appropriate are visually and audibly alarmed on the device function display screen 68. A digital camera 69 may also be utilized to aid the monitoring process visually tracking the wound closure progress.

What is claimed is:

1. A tissue oxygenation system that aids in the healing of damaged tissue comprising:
    an electrochemical oxygen concentrator for generating oxygen;
    a microprocessor for variably adjusting oxygen flow from said concentrator to said damaged tissue;
    a pressure sensing system outputting pressure information to said microprocessor;
    a temperature monitoring system outputting temperature information from said damaged tissue to said microprocessor;
    a power delivery system controlled by said microcontroller to deliver variable power to the concentrator;
    a tubing having a distal end and a proximal end and connected to the concentrator to receive said oxygen and deliver said oxygen to said damaged tissue; and
    a temperature sensor disposed in said tubing and in communication with said temperature monitoring system;
    wherein said proximal end of said tubing is removably connected to said concentrator and the distal end of said tubing is placed adjacent said damaged tissue such that said temperature sensor is positioned adjacent said damaged tissue; a moisture absorbent dressing is positioned adjacent said distal end of said tubing on said damaged tissue; and a reduced moisture vapor permeable dressing system positioned over and covering said moisture absorbent dressing, said distal end of said tubing, and said damaged tissue thereby forming a restricted airflow enclosure; and
    wherein the microprocessor is operable, in response to the pressure information received from the pressure sensing system, to control the power delivery system to vary the oxygen flow generated by the concentrator and provided through the tubing to the restricted airflow enclosure.

2. The tissue oxygenation system of claim 1, wherein said distal end of said tubing comprises a generally flat, oxygen-permeable tape section.

3. The tissue oxygenation system of claim 1, wherein said microprocessor is capable of receiving user input data.

4. The tissue oxygenation system of claim 1,
    wherein said temperature monitoring system outputs said temperature information from said temperature sensor to said microprocessor;
    wherein the microprocessor is operable to vary the oxygen flow generated by the concentrator and provided to the restricted airflow enclosure in response to the temperature information received from the temperature monitoring system.

5. A method for treating damaged tissue comprising the steps of:
    connecting a tubing between an electrochemical oxygen concentrator and damaged tissue to receive oxygen and deliver the oxygen to said damaged tissue, wherein a proximal end of said tubing is removably connected to said concentrator and a distal end of said tubing that includes a temperature sensor disposed in said tubing is placed adjacent said damaged tissue such that the temperature sensor is located adjacent said damaged tissue;
    positioning a moisture absorbent dressing adjacent said distal end of the tubing on said damaged tissue;
    positioning a reduced moisture vapor permeable dressing system over and covering said moisture absorbent dressing to provide a restricted airflow enclosure adjacent said distal end of said tubing and said damaged tissue
    generating oxygen using the concentrator and providing the oxygen to the restricted airflow enclosure adjacent said damaged tissue;
    determining a pressure adjacent said damaged tissue;
    determining a temperature adjacent said damaged tissue using the temperature sensor;
    using a microprocessor to variably adjust oxygen flow from said concentrator to said damaged tissue in response to the determined pressure; and
    using a power delivery system controlled by said microprocessor to vary power to said concentrator in order to variably adjust the oxygen flow.

6. The method of treating damaged tissue of claim 5, wherein said distal end of said tubing comprises a generally flat, oxygen permeable tape or membrane section.

7. The method of treating damaged tissue of claim 5, wherein said microprocessor is capable of receiving user input data.

8. The method of treating damaged tissue of claim 5, further comprising:
    using the microprocessor to variably adjust the oxygen flow from said concentrator to said damaged tissue in response to the determined temperature.

9. The tissue oxygenation system of claim 1, wherein the microprocessor is operable to monitor the oxygen flow rate from the oxygen concentrator and, in response to determining that the oxygen flow rate is not a desired flow rate, adjust a current to the oxygen concentrator to adjust the oxygen flow rate from the oxygen concentrator.

10. The method of treating damaged tissue of claim 5, further comprising:
    monitoring the oxygen flow rate from the concentrator;
    determining that the oxygen flow rate is not a desired flow rate; and
    adjusting a current to the concentrator to adjust the oxygen flow rate.

* * * * *

UNITED STATES PATENT AND TRADEMARK OFFICE
CERTIFICATE OF CORRECTION

PATENT NO. : 8,287,506 B2  
APPLICATION NO. : 12/288873  
DATED : October 16, 2012  
INVENTOR(S) : Michael C. Wells et al.

Page 1 of 1

It is certified that error appears in the above-identified patent and that said Letters Patent is hereby corrected as shown below:

Column 5, line 1 needs amended to:

change data reading:
"as, example, anoxygen partial pressure sensor, at the wound"

to read:
--as, for example, an oxygen partial pressure sensor, at the wound--

Signed and Sealed this
Twenty-ninth Day of January, 2013

David J. Kappos
*Director of the United States Patent and Trademark Office*